(12) United States Patent
Bogoch

(10) Patent No.: US 7,658,935 B2
(45) Date of Patent: Feb. 9, 2010

(54) METHODS AND COMPOSITIONS FOR STIMULATING THE IMMUNE SYSTEM

(76) Inventor: Samuel Bogoch, 49 E. 91st St., New York, NY (US) 10028

( * ) Notice: Subject to any disclaimer, the term of this patent is extended or adjusted under 35 U.S.C. 154(b) by 430 days.

(21) Appl. No.: 09/854,568

(22) Filed: May 15, 2001

(65) Prior Publication Data

US 2002/0045187 A1 Apr. 18, 2002

Related U.S. Application Data

(60) Continuation of application No. 08/031,562, filed on Mar. 16, 1993, which is a continuation-in-part of application No. 07/744,649, filed on Aug. 8, 1991, now abandoned, which is a continuation of application No. 07/227,621, filed on Aug. 3, 1988, now abandoned, which is a continuation of application No. 06/281,883, filed on Jul. 9, 1981, now Pat. No. 4,976,957, and a continuation-in-part of application No. 06/019,078, filed on Mar. 9, 1979, now abandoned, which is a continuation-in-part of application No. 05/941,940, filed on Sep. 13, 1978, now abandoned, which is a continuation-in-part of application No. 05/922,799, filed on Jul. 7, 1978, now Pat. No. 4,298,590, and a division of application No. 05/852,200, filed on Nov. 17, 1977, now Pat. No. 4,196,186, which is a continuation of application No. 04/621,112, filed on Oct. 9, 1975, now abandoned, which is a continuation-in-part of application No. 04/553,075, filed on Feb. 25, 1975, now abandoned, which is a continuation-in-part of application No. 04/550,432, filed on Feb. 18, 1975, now abandoned, which is a continuation-in-part of application No. 04/450,404, filed on Mar. 12, 1974, now abandoned, which is a continuation-in-part of application No. 04/385,451, filed on Aug. 3, 1973, now abandoned.

(51) Int. Cl.
*A61K 38/00* (2006.01)

(52) U.S. Cl. .................. 424/277.1; 530/300; 530/350

(58) Field of Classification Search ............ 424/277.1; 435/7.23; 436/813; 530/325, 395, 300, 350
See application file for complete search history.

(56) References Cited

U.S. PATENT DOCUMENTS 4,840,915 A * 6/1989 Bogoch ................ 436/530
4,877,611 A 10/1989 Cantrell ................ 424/88
4,976,957 A * 12/1990 Bogoch ................ 530/389.7
5,156,841 A 10/1992 Rapp ................ 424/88
5,866,690 A * 2/1999 Bogoch ................ 530/388.15
2007/0160624 A1 * 7/2007 Bogoch et al. ........... 424/190.1

FOREIGN PATENT DOCUMENTS

EP 0015755 A1 * 9/1980

OTHER PUBLICATIONS

Williams et al, Methods in Immunology and Immunochemistry, Academic Press, 1967, pp. 211-215.*
Ezzell, The Journal of NIH Research, 7, 46-49, 1995.*
Spitler, Cancer Biotherapy, 10, 1-3, 1995.*
Bogoch et al. (Neurochem. Res. 1979; 4 (4); 465-472).*
Bogoch S. (1976). Brain Glycoproteins and Recognition Functions: Recognins and Cancer. In Volk BW and Schneck L (eds): "Current Trends in Sphingolipidoses and Applied Disorders". New York: Plenum Press, pp. 555-566.*
Jean-Claude Bystryn: *Tumor Vaccines*; Cancer and Mestastasis Review 9:81-91, 1990.
Freda K. Stevenson: Update on Tumor Vaccines; Int. J. Clin Lab Res 22:84 89, 1992.
Bogoch et al.: Tumor Markers: Malignin and Related Recognins Associated with Malignancy Rather Than With Cell Type; Neurochemistry and Clinical Neurology, pp. 407-424, Alan R. Liss, Inc. 1980.
Freda K. Stevenson: *Tumor Vaccines*, The FASEB Journal, vol. 5, Jun. 1991, pp. 2250-2257.
Jerrold H. Zar: *Biostatistical Analysis*, Prentice-Hall, Inc., Englewood Cliffs, NJ, second edition, 1984, p. 278.
Bogoch et al.: *Elevated Levels of Anti-Malignin Antibody Are Quantitatively Related to Longer Survival in Cancer Patients*; Prognosis, pp. 739-747, 1984.
H. Masui et al., entitled, "Cytotoxicity against Human Tumor Cells Mediated by the Conjugate of Anti-Epidermal Growth Factor Receptor Monoclonal Antibody to Recombinant Ricin A Chain", Cancer Research, vol. 49, Jul. 1, 1989, pp. 3482-3488.

* cited by examiner

*Primary Examiner*—Stephen L Rawlings
(74) *Attorney, Agent, or Firm*—Kenyon & Kenyon LLP

(57) ABSTRACT

Methods for stimulating the immune system of an individual to produce and release antimalignin antibody are disclosed. The method comprises administering an amount of a composition containing malignin, recognin M, recognin L, or a peptide having the immunological specificity thereof. Also disclosed is a device for removing cancer cells from the body of a subject.

5 Claims, 3 Drawing Sheets

METHODS AND COMPOSITIONS FOR STIMULATING THE IMMUNE SYSTEM

CROSS REFERENCES TO OTHER APPLICATIONS

This application is a continuation of and claims priority to application Ser. No. 08/031,562, filed Mar. 16, 1993; which is a continuation-in-part of application Ser. No. 07/744,649, filed Aug. 8, 1991, abandoned, to which the instant application also claims priority. Application Ser. No. 07/744,649 is a continuation of application Ser. No. 07/227,621, filed Aug. 3, 1988, abandoned; which is a continuation of application Ser. No. 06/281,883, filed Jul. 9, 1981, now U.S. Pat. No. 4,976,957; which is a continuation-in-part of application Ser. No. 05/922,799, filed Jul. 7, 1978, now U.S. Pat. No. 4,298,590, and application Ser. No. 06/019,078, filed Mar. 9, 1979, abandoned; application Ser. No. 06/019,078 is a continuation-in-part of application Ser. No. 05/941,940, filed Sep. 13, 1978, abandoned; which is a continuation of application Ser. No. 05/852,200, filed Nov. 17, 1977, now U.S. Pat. No. 4,196,186; which is a continuation of application Ser. No. 04/621,112, filed Oct. 9, 1975, abandoned; which is a continuation-in-part of each of application Ser. No. 04/553,075, filed Feb. 25, 1975, abandoned, application Ser. No. 04/550,432, filed Feb. 18, 1975, abandoned, application Ser. No. 04/450,404, filed Mar. 12, 1974, abandoned, and application Ser. No. 04/385,451, filed Aug. 3, 1973, abandoned. All applications listed above are incorporated herein by reference.

THE INVENTION

This invention is directed to the discovery of products and methods to aid in the prevention of cancer, or its treatment, through the administration of a vaccine, or of the products produced by the vaccine, to destroy or inhibit the growth of cancer cells regardless of cell type.

The present invention teaches two ways of strengthening immune defenses against cancer: the administration of either 1) a specific antibody (anti-Recognin) itself, or 2) a derivative of a Recognin, to produce both the antibody and the cellular part of the immune response—thus a vaccine for cancer.

In 1959, Dr. Lewis Thomas, and later Dr. MacFarlane Burnet theorized that there might be an ongoing immune process throughout normal life—immunosurveillance—to detect and destroy any cancer cells which might arise. However, there was no evidence to support this theory. In recent years, indirect evidence has suggested that immune processes somehow protect people from acquiring cancer. But until now there has been no direct evidence of these processes in humans. Thus for example some such process might be assumed to exist because in immunodeficient disorders as AIDS, the incidence of cancer is markedly increased. However, in these immunodeficient disorders where there are causative agents such as the HIV virus, the increased incidence of cancer might be due to a carcinogenic effect of the virus itself on cells which, since the Rous sarcoma virus, has been known to exist for several viruses. Therefore, because of the lack of any direct evidence of immunosurveillance in humans, the idea has been largely abandoned.

It was therefore totally unexpected to find in the present invention that the anti-Recognin antibody increases in concentration with age in healthy non-tumor bearing individuals between the third and the seventh decades as the risk of cancer increases. The anti-Recognin increases even more when clinical cancer appears. In the present discovery, the antibody also was shown to return to normal when the cancer is successfully treated.

In the present invention, the anti-Recognin also was shown to kill or inhibit the growth of cancer cells.

In addition, Anti-Recognin was found bound to cancer cells removed at surgery or at autopsy.

While anti-Recognin was shown to be elevated during the presence of clinical cancer, there was no evidence to suggest that anti-Recognin functions to protect humans against cancer before it becomes clinically evident. Therefore there was no reason to assume that the development of a vaccine composed of a Recognin or its derivatives would protect against the development of clinical cancer, or help to destroy it once it had begun. The present invention describes products to aid both cancer prevention and cancer treatment.

Cancer treatment is most successful when the cancer is detected early. Anti-Recognin antibody increases in concentration with a wide variety of cancer cell types, rather than just a particular cell type, and is quantitatively related to survival in patients.

Cancer development involves the "transformation" of the cells to the malignant state and the "proliferation" or the multiplication of the transformed cells. The malignant cells multiply out of control until they become a palpable mass, or erode a blood vessel causing bleeding. The mass or bleeding may be the first clinical symptoms of cancer. Until now, there has been no way to know when transformation has occurred except by performing microscopic examination of tissue taken during surgical biopsy. In seeking to detect and treat breast cancer, for example, women are advised to examine their breasts regularly for lumps. According to the American Cancer Society (ACS), by the time a lump can be felt, the cancer has progressed further than is ideal for treatment; Therefore the ACS advise regular mammograms. But from a recent conference at the National Cancer Institute in Bethesda, it appears that mammograms do not help the survival rate at all for women below the age of 50, and only improve survival approximately 30% after 50 years of age.

Mammography and other cancer detection techniques can now be assisted by the blood test for the concentration of anti-Recognin antibody. An increase in this antibody occurs in over 900 of patients with early breast cancer. The antibody may be elevated when the breast cancer is so small that it is missed on biopsy examination. Two such missed tumors were detected on reexamination of biopsy specimens. In another group of 170 normal individuals, only five had elevated anti-Recognin tests. Four of these five (three in their 30s) developed cancer in sites other than the breast within three years.

Cells which have undergone malignant transformation in humans may take years to, or may never, proliferate to become clinical cancer[1]. If inhibition of proliferation is an immune process, as has been theorized[2,3] there is no direct evidence in human cancer of such an immune process, and the responsible mechanisms are unknown. Anti-Recognin, specific for highly antigenic 10K cancer cell membrane oncoproteins[4-6], is a human IgM antibody which increases in concentration in clinical cancer regardless of cell type, and is quantitatively related to survival in patients[7-13]. In vitro, antigen-purified human anti-Recognin is here shown to be present in non-saturating amounts on cancer cells removed at surgery or autopsy, to be cytotoxic to malignant glial cells, and inhibitory to the growth of small cell lung carcinoma cells at picograms of antibody per cell. In vivo, anti-Recognin concentration is shown in healthy humans without tumors to increase each decade between the fourth and the seventh; to increase markedly at the diagnosis of breast cancer; then to have returned to the normal range 0.1 to 27 years after successful treatment. Taken together, these properties suggest that anti-Recognin is a general inhibitory transformation antibody whose augmentation may be useful in efforts at the immune prevention and treatment of cancer.

In glioblastoma, the normal 250,000 Dalton membrane glycoprotein 10B which has been associated with recognition phenomena in the brain[14] is replaced by the Recognin precursor glycoprotein, which has 50% less carbohydrate and is overproduced 7 to 10 fold relative to the concentration of 10B in normal brain[4-7]. When malignin was produced as the immunogenic fragment of the precursor it was thought to be a cell-type-specific cancer marker[4]. It was only when similar 10K peptides with identical immunoreactivity were produced from MCF7 breast cancer cells (Recognin M) and from P3J lymphoma (Recognin L)[5] that malignin appeared to be a more general cancer antigen. An antibody to Recognin was shown to be elevated in patients with brain malignancies, both primary and secondary[14], and then surprisingly, elevated in all other malignancies tested[10-13]. The notion of a general cancer antigen and antibody was difficult to accept. However, this conclusion was supported by the demonstration that anti-Recognin was increased in concentration in patients with a wide variety of cell types of cancer in 3,315 serum specimens from cancer patients and controls determined blind by three independent laboratories[10-13]. Anti-Recognin has been isolated from human serum[6] produced in mouse monoclonal form[9], and produced in vitro by human lymphocytes challenged by the antigen Recognin[8]; and in all these cases has been shown to be an IgM[8].

REFERENCES CITED IN TEXT, EXAMPLES, AND LEGENDS FOR FIGURES

1. Cohen, P. et al. *Prostate* 6 (4), 437-443 (1985).
2. Thomas, L. Discussion of paper by P. B. Medawar, in *Cellular and Humoral Aspects of Hypersensitivity* (ed. H. S. Lawrence) 529 (Hober-Harper N.Y., 1959).
3. Burnet, M. *Cellular Immunology*, 252-286 (Melbourne University Press, Cambridge University Press, 1969).
4. Bogoch, S. Mon *Natnl. Cancer Institute* 46, 133-137 (1977).
5. Bogoch, S. & Bogoch, E. S. *Neurochemical Research* 4, 467-473 (1979).
6. Bogoch, S. and Bogoch, E. S. *Lancet* 1, 987(1979).
7. Bogoch, S. and Bogoch, E. S. *Protides of Biological Fluids* 30, 337-352 (1983).
8. Bogoch, S., Bogoch, E. S. & Iliescu, V. M. *Cancer Detection and Prevention* 12, 312-320 (1988).
9. Bogoch, S, Bogoch, E. S. and Tsung Y-K. *Lancet* 2, 141-142 (1981).
10. Thornthwaite, J. T., Derhagopian, R. and Reimer, W. *Proc. Annu. Meet. Am. Assoc. Cancer Res.* 31, A1550 (1990).
11. Bogoch, S. and Bogoch, E. S. *Lancet* 337, 997 (1991).
12. Bogoch, S., et al. *J. Med.* 13, 49-69, 1982.
13. Bogoch, S., et al. *Protides of Biological Fluids* 31, 739-747 (1984).
14. Bogoch, S. *The Biochemistry of Memory: with an inquiry into the function of the brain mucoides* (Oxford University Press, 1968).
15. Bogoch, S. U.S. patent application Ser. No. 07/744,649.
16. Bogoch, S. and Bogoch, E. S. *Perspectives in immunology* (ed. S. E. Rosenberg) 693-696 (Academic Press, New York, 1980).
17. Redmond, F. A. Doctoral Thesis, Medical College of Ohio at Toledo, 1980.

This figure is divided into 12 sections, labelled "a" through "l". Sections "a" through "i" of this figure demonstrate the specificity of the attachment to (and when combined with a histological stain, the specificity of staining of) malignant cells of various cell types by anti-Recognin antibody. Sections "j", "k" and "l" demonstrate that anti-Recognin antibody is cytotoxic to malignant cells. (see full description under Example 1).

FIG. 2

This figure quantitates the inhibition of malignant cell growth and/or cytotoxicity to malignant cells by anti-Recognin antibody. By serial dilution of the antibody it is determined that the antibody is cytotoxic to malignant cell growth in concentrations of picograms per cell. (see full description under Example 6).

FIG. 3

This figure demonstrates three things: 1) in healthy individual humans without tumors, the concentration of anti-Recognin antibody increases with age as the risk of clinical cancer increases; 2) the concentration of anti-Recognin antibody increases markedly in individuals with proven human breast cancer; and 3) the concentration of anti-Recognin antibody returns to normal concentrations after successful treatment of human breast cancer. (see full description under Example 7).

EXAMPLE-1

Figure 1A:
FIG. 1
Figure 1B:
Figure 1C:
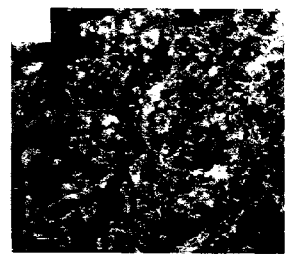
Figure 1D:
Figure 1E:
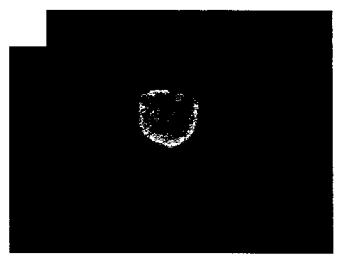
Figure 1F:
Figure 1G:
Figure 1H:
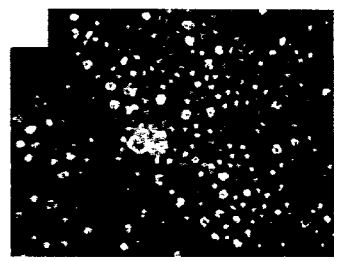
Figure 1I:

To test further whether anti-Recognin is indeed an antibody specific to the process of malignancy rather than to a particular cell type, and to malignancy only, Recognin was demonstrated immunocytochemically in several cell types of malignancy. FIG. 1, *a* through *l, g*, shows the Recognin to be localized in cytoplasmic and outer cell membranes. FIGS. 1*h* and 1*i* show the specificity of anti-Recognin in binding selectively to two blast cells, but not to normal red and white blood cells in the same smear.

Legend for FIG. 1: Immunostaining of malignant cells with antimalignin antibody. a. squamous cell carcinoma of lung, cells obtained by bronchial washing; b. scirrous carcinoma of breast, fresh frozen section; c. retrobulbar malignant neuroectodermal tumor, fresh frozen section; d. carcinoma of pancreas, MIAPACA cell culture; e. lymphoma, single cell from pleural fluid; f. carcinoma of the vulva cells, frozen smear; g. small cell carcinoma of lung, alkaline phosphatase stain; h. acute lymphatic leukemia, two blast cells in blood smear, both fluorescent and natural light are on together; i. same slide as in h., but with natural light turned off and only fluorescent light on; j., k., and l. cytotoxicity of 50 microliters of anti-Recognin antibody, 10 micrograms/ml, left in contact for varying periods of time with glioblastoma brain cancer cells growing on wall of tissue culture flask: j. 30 minutes at 50 C.; k. 45 minutes at room temperature; l. one hour at room temperature, before the second layer for visualization was applied.

METHODS. Tissue specimens removed at surgery or autopsy were embedded in OCT gel on cryomold specimen molds and cryostat sections approximately 7-8 microns thick were placed on standard glass slides and kept at −20° C. for at least 24 hours before use. Alternatively, tissue was deposited on the slide by "touch prep" technique and either immediately stained or fixed with 100% acetone or 95% ethanol at 4° C. before staining. 50 microliters of antimalignin antibody, 10 microgram per ml, purified by adsorption to immobilized malignin as in the method for its quantitative determination in the legend for Table 1, or of PBS for controls, was applied to the section for 30 minutes at 4° C., rinsed in 0.5 M Tris buffer for five minutes at room temperature. For visualization, either a) a second layer of fluorescein labeled goat anti-human immunoglobulin was applied for one hour, rinsed in 0.5 M Tris buffer for five minutes at room temperature, and the slide viewed with light and fluorescent microscopy; or b) an alkaline phosphatase method of visualization was used.

EXAMPLE 2

While anti-Recognin given intravenously has been shown to bind preferentially to malignant glioma cells in the rat brain in vivo[7] it was not known whether the antibody actually binds to cancer cells in humans in vivo. Human cancer tissue freshly excised at surgery and at autopsy was therefore examined for the presence of anti-Recognin antibody[15]. Table 1 shows that anti-Recognin can be eluted from these tissues. All of the exposed Recognin sites are not covered by antibody since before antibody elution cancer cells can be immunostained with anti-Recognin (FIG. 1).

| | | | ug/ml medium or buffer /mg tissue, mean +/− S. D. | |
|---|---|---|---|---|
| Fluant | Tissue | N | Slow-Binding Antibody (2 Hours) | Fast-Binding Antibody (10 Minutes) |
| L15 medium | Cancer | 6 | 0.97 +/− 0.65 | 0.47 +/− 0.5 |
| | Normal | 4 | 0.10 +/− 0.14 | 0.14 +/− 0.12 |
| Glycine buffer, pH 2.4 | Cancer | 3 | 0.27 +/− 0.12 | 0.36 +/− 0.17 |
| | Normal | 2 | 0.02 +/− 0.02 | 0.03 +/− 0.04 |

Legend for Table in Example 2: METHODS. Normal tissue (muscle, liver and brain), and cancer tissue (adenocarcinoma, transitional cell carcinoma, neuroblastoma, and lymph node metastases) removed at surgery and autopsy was placed in sterile Leibovitz Medium L15 plus antibiotics, (Penicillin-Streptomycin-Fungizone Mixture, 1 ml/100 ml. of medium) (Grand Island Biological Co., Grand Island, N.Y.). Approximately 5 mm cubed pieces of tissue were trimmed of extraneous material, weighed in sterile plastic Petri dishes, and minced into less than 1 cu mm pieces with sterile blades, then suspended in either 5 ml of L15 medium for 2 hours, or in 5 ml of glycine buffer pH 2.4 for 15 minutes, cultured at 37° C. in a humid container. N refers to the number of separate tissue specimens studied with each eluant. Each eluant was coded for blind determination, shipped overnight in dry ice to the laboratory, and the next day, quantitatively determined for antimalignin antibody determined with immobilized malignin antigen (TARGET reagent, Brain Research, Inc., Boston). In the preparation of TARGET reagent, as previously described[15], human glioblastoma cells were grown in 250 ml sterile tissue culture flasks stacked in the horizontal position in a 37° C. incubator until a monolayer of cells had covered the wall of the flask, freed from the wall with trypsin, scraped with spatula into a glass beaker, homogenized with a Branson sonifier, dialyzed, concentrated by perevaporation, centrifuged, chromatographed on a Cellex D column with stepwise elution with buffered solutions of decreasing pH, with the protein in each eluate quantified by adsorption at 280 mu. The last eluate, which contains malignin eluted at its pK of approximately 2.7, was rechromatographed. The final preparation contained malignin with the following composition: Glu13Asp9Thr5Ser5Pro4Gly6Ala7Val6Met2Ileu4Leu8 Tyr3Phe3His2Lys6Arg51/2Cys1, and demonstrating a molecular weight of approximately 10K; and dimers and trimers thereof, on SDS gel and thin layer gel chromatography. Malignin was combined covalently with bromoacetylcellulose to produce immobilized TARGET reagent. To quantify the antimalignin antibody in cancer and normal tissue eluants, 0.2 ml samples of each eluant, in duplicate, were exposed to TARGET reagent with shaking for either two hours or 10 minutes, the bound antibody washed three times with cold NaCl, then released from the antigen by incubation with shaking with 0.25 molar acetic acid, centrifuged at 3000 rpm, the clear acetic acid supernatant read spectrophotometrically at O.D. 280, and the results converted to micrograms of protein. Results are given, as mean+/−S.D. for each group of tissues and each eluant, for slow-binding antibody (2 hour contact of eluant with immobilized malignin) and fast-binding antibody (10 minute contact of eluant with immobilized malignin), microgram/ml eluant/mg. original tissue[16].

EXAMPLE 3

That anti-Recognin is an IgM has been confirmed by the quantitation of human serum anti-Recognin in a luminescent plate assay by reacting the bound anti-Recognin with goat anti-human IgM specific for mu chains.

EXAMPLE 4

Figure 3:
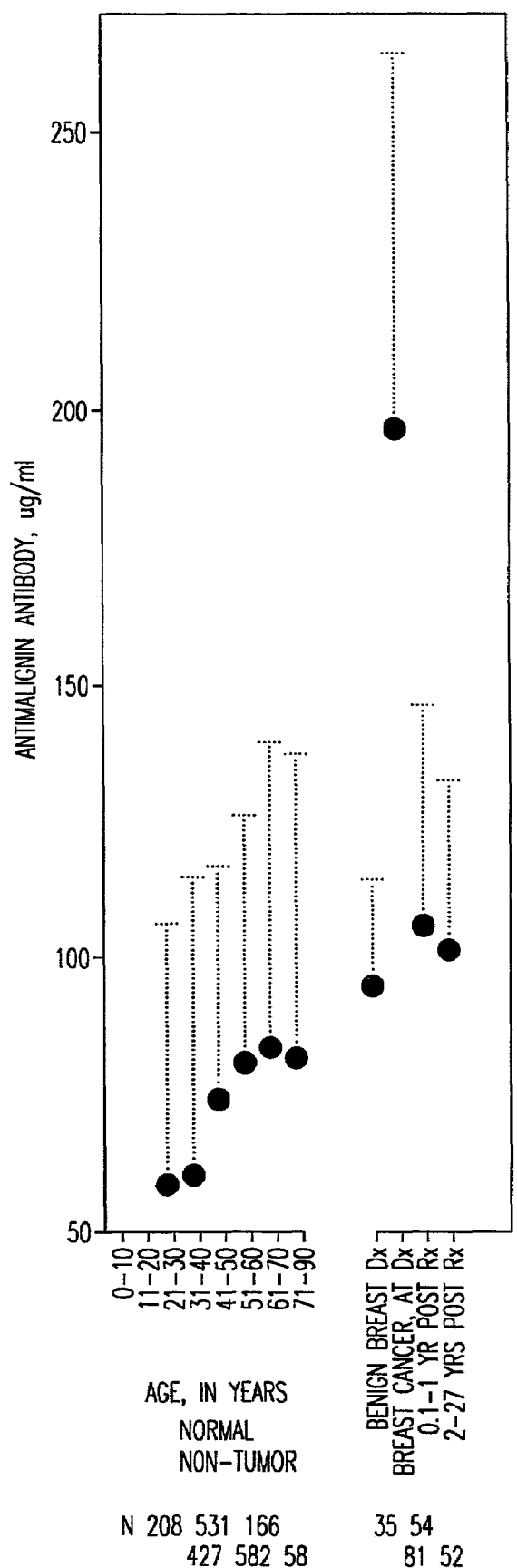

To determine whether other IgMs would bind to Recognin, 7 mg. of non-specific serum IgM (Sigma) was added to 20 micrograms of immobilized Recognin malignin as in the method described in the legend for Table in EXAMPLE 2; only 200 nanograms of this nonspecific serum IgM was bound, in contrast to >500 micrograms of anti-Recognin IgM (FIG. 3).

EXAMPLE 5

Figure 1J:
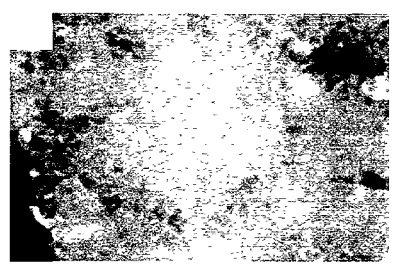
Figure 1K:
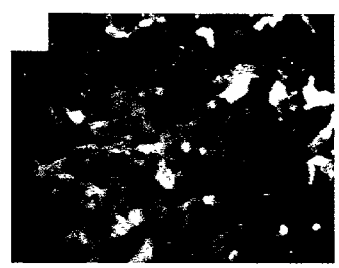
Figure 1L:

The effect of anti-Recognin on cancer cells in vitro is demonstrated by its cytotoxicity (FIG. 1j through 1l).

EXAMPLE 6

The effect of anti-Recognin on cancer cells in vitro is demonstrated by its growth inhibition properties (FIG. 2) which occur in the range of picograms/cell.

Figure 2:
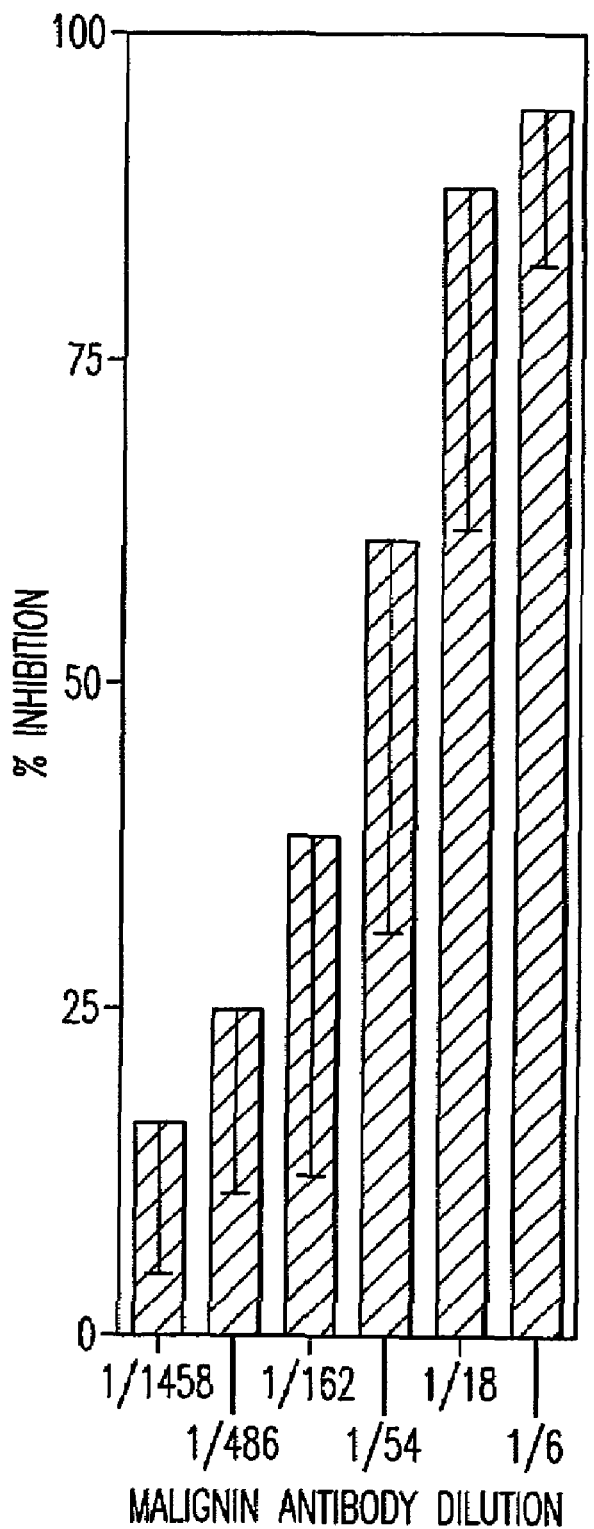

LEGEND FOR FIG. 2 in EXAMPLE 6: Inhibition of growth of small cell lung carcinoma cells in vitro by anti-Recognin antibody. The inhibition is proportional to the concentration of anti-Recognin, which was 50% effective in the picogram per cell range. Each bar in the Figure represents the mean+/−SD for 24 wells, that is, from 3 wells for each of eight separate preparations of anti-Recognin at each dilution. METHODS. Small Cell Lung carcinoma cell line UCHNCU, grown in suspension and maintained in RPMI 1640 10% FCS (fetal calf serum) was seeded in 96 well microtitre plates (round bottom) at 104 cells per well. Serial dilutions were made of anti-Recognin antibody which had been purified by adsorption to immobilized malignin so that final concentration of anti-Recognin in RPMI Fes was 116 to 1/1458; final total volume per well was 200 microlitres. Plates were incubated at 37° C. in 6% $CO_2$/air for 3 days. On day 3, cultures were pulsed with 1 uci/well tritiated thymidine (3HTdR for 6 hours), then cultures were harvested with automatic cell harvester on filter pads. Filters were dried for 2 hours in 37° C. dry incubator, discs were placed into scintillation vials, 2 ml OPTIPHASE scintillant added, tubes capped cpms counted on Beckman LS 1800 BETA COUNTER and % Inhibition calculated as Control-Experimental/Control×100.

EXAMPLE 7

That humans who do not have benign or malignant tumors have appreciable anti-Recognin antibody in their serum[4,10-13] requires explanation. We have now discovered that the concentration of this antibody in non-tumor bearing humans increases with age (FIG. 3).

LEGEND FOR FIG. 3 in EXAMPLE 7. Increase in concentration of serum anti-Recognin (antimalignin) antibody with age in individuals without tumors, and in human clinical breast cancer; and its return to normal after successful treatment. Each data point represents the mean (+/−standard deviation) concentration of antimalignin antibody. "N" indicates the number of specimens per data point. "Age in years, Normal Non-Tumor": specimens from normal individuals without benign or malignant tumors: from the left, the first five points are one for each decade of age from the 3rd through the 7th; the sixth point is for ages 71-90. The 7th through 10th points represent 4 clinical states. 7th point: "Benign Breast Ox (Diagnosis)"—patients with a variety of mammographic anomalies judged benign on cytopathological examination; 34/35 were in the normal range of antibody concentration (135 ug/ml) (see text for discussion of "false positive" results). 8th point: "Breast Cancer at Dx (Diagnosis)": patients at time of diagnosis of breast cancer; these were all in the elevated range (135 or > ug/ml). 9th and 10th points: "Post Rx" data are 0.1 to 1 year, and 2 to 27 years respectively after successful treatment of breast cancer. The ages in years (mean+/−SD) of the patients for the 7th through 10th points were respectively 47.3(+/−11), 56.2(+/−12), 51.0(+/−11), and 53.2(+/−13).

METHODS: 2,194 specimens were received at random from centres in the US and 2 in the UK. Determinations were performed blind in three independent laboratories. All specimens were collected in unsiliconized ED #6440 VACUTAINER tubes (Becton Dickinson Co.), the sera shipped in dry ice and determined blind within 24 hours by reacting 0.2 ml of serum with immobilized malignin in duplicate as previously described (see legend for Table in EXAMPLE 2).

An increase with age of a cancer-related immune mechanism, in this case an antibody inhibitory to cancer cells, in the non-cancer normal population to our knowledge has not previously been described. That this increase is temporally correlated stepwise with the increased risk for developing cancer with increasing age suggests that its function is what it appears to be: that is, part of an immunosurveillance process for which hitherto there has been no direct evidence in humans. Either genetically programmed and anticipatory, or simply as a continuing response to the appearance of the transformation antigen Recognin, the anti-Recognin antibody response could accompany the intermittent or continuous appearance of transformed cells, with the resultant suppression of these cells (see FIG. 2). This normal inhibitory activity might be increased in benign tumors, a state of cell hyperplasia in which the frequency of transformation would be expected to be greater than normal (see data below, and FIG. 3). The proliferation of transformed cells would result in the marked elevation in anti-Recognin concentration above normal levels, and clinical evidence of cancer. This is seen to occur in breast cancer at the time of diagnosis (FIG. 3). FIG. 3 also shows that marked elevation of anti-Recognin is not stigmatic, but disappears after successful treatment; in 83% of patients from 0.1 to 1 year after treatment, and in 96% of patients from 2 to 27 years after treatment resulting in 'no clinical evidence of cancer', whether achieved by surgery or other therapy.

One limitation of studies which correlate anti-Recognin levels before biopsy with cytopathological findings at biopsy is that anti-Recognin may be elevated when the malignancy is small enough to be missed on cytological examination, as when the tumor is only 1 mm in diameter[10] or smaller, as 1) in the present study where only a few malignant ducts were seen in one corner of one section, 2) in two such breast tumors out of seven proven to be malignant only on repeated examination and 3) possibly but not proven in 12 of 22 cases of breast tumor judged benign on cytology. That such supposed 'false positive' anti-Recognin elevations may represent early warning of malignancy is illustrated by a group of 170 healthy individuals first studied in 1988-89 of whom only five had elevated antibody (2.3%): four of these five (of whom three were in their 30s) developed clinical cancer within three years.

These results clearly indicate a process for quantitatively assessing the immune status of an individual human or animal with regard to the level of their anti-cancer defenses, and with regard to whether malignant cells are present or not, by determining the quantity of anti-Recognin antibody and the quantity of immune cells specific for malignin and Recognins L and M in their serum or other body fluids or tissues.

Since anti-Recognin increases in concentration with age in non-tumor bearing humans, is markedly elevated when transformed cells are clearly present, and this elevation disappears when there is no longer evidence of the presence of transformed cells, we have called anti-Recognin a transformation antibody; to our knowledge the first so described. The antigen is not restricted to one cell type; the antibody is general. The earlier finding by actuarial survival studies that the duration of survival in cancer patients is quantitatively related to the concentration of anti-Recognin[12,13], taken with the present demonstration that anti-Recognin is cytotoxic and inhibitory to cancer cells, and that some but not all sites on cancer cells in vivo are covered by anti-Recognin, together indicate that an effort to augment this inhibitory antibody by administering the human antibody itself, or a derivative of a Recognin (a derivative of malignin, Recognin L or Recognin M) as vaccine to stimulate both the cellular and humoral elements, can be useful in efforts at the immune prevention and therapy of cancer.

EXAMPLE 8

The Recognin derivative vaccine can be any product larger, smaller or the same molecular weight which contains the immunological specificity of malignin, Recognin L or Recognin M, (see application Ser. No. 07/744,649, now abandoned, and the applications of which it is a continuation-in-part as listed above incorporated herein by reference) can be used. The vaccine can be entirely produced from tissues or cells, or it may be entirely synthetic, or any combination of the two. For example the Recognin derivative vaccine malignin glycoprotein precursor, molecular weight approximately 250,000 Daltons, or any fraction thereof which contains the immunological specificity of malignin, Recognin L or recognin M can be administered as vaccine to individual humans or animals for example, but not exclusively, in doses of approximately 1 mg or more subcutaneously, and the quantity of anti-Recognin determined by the methods shown in Example 2 as well as changes in immune cells, such as B cells, T-cells, both helper and suppressor, macrophages, before and after the administration of vaccine. The level of anti-Recognin will increase approximately 10 days after the first administration of vaccine. Regardless of whether the increase has occurred, a second dose of vaccine is given after the blood specimen is taken for anti-Recognin determination, and 10 days later, a third blood specimen is taken for anti-Recognin determination and a third dose of vaccine is administered. Thirty days after the first dose of vaccine is administered, the anti-Recognin level should be at a maximum. Additional booster doses of vaccine may be given to maintain the level of antibody achieved and depending upon the degree of risk of cancer exhibited by the subject. For example in a family in which the grandmother, mother, and each of the two sisters have developed breast cancer, for the remaining sister who is receiving the vaccine the physician in charge may decide that more frequent boosters are required. Where the vaccine is used for prevention, the changes in anti-Recognin and immune cells will be followed. Where the vaccine is used in treatment of already present clinical cancer, all clinical and laboratory determinations appropriate to the type of cancer and its stage (e.g. CATSCANs, MRI, blood counts in hematological malignancies, etc.) also will be followed for evidence of beneficial effect.

EXAMPLE 9

The administration of a product such as DNA or RNA to humans or animals which is specific for the production of a Recognin or a derivative thereof, which contains the immunological specificity of malignin, Recognin L or Recognin M, if such DNA or RNA is administered so as to be incorporated by the genome or the protein, synthesizing apparatus respectively, this will in turn cause to be inhibited or destroyed cancer cells, regardless of cell type, and prevent the development of clinical cancer, or if it has already developed, treat clinical cancer.

EXAMPLE 10

The administration of a product which has the characteristics of an antibody to malignin and the Recognins L and M will cause to be inhibited or destroyed cancer cells, regardless of cell type, and prevent the development of clinical cancer, or if it has already developed, treat clinical cancer. This product can be the whole antibody of a fragment thereof, the antibody alone, or bound to an additional agent which is cytotoxic to cancer cells.

EXAMPLE 11

A product which has the characteristics of a cell or mechanism with immunological specificity for malignin and the Recognins L and M, where the cell is any cell which will destroy or inhibit the growth of cancer cells such as a T cell, a B cell, a phagocytic cell, or a device or mechanism which when in contact with cancer cells would bind, adsorb or engulf them so as to destroy them and/or remove them from the body such as a filter or column or resin or surface through which or on which the cancer cells are made to pass or come in contact, is useful to treat clinical cancer.

EXAMPLE 12

Production of Purified MALIGNIN Product from Crude MALIGNIN-Containing Fraction

A crude malignin-containing fraction is prepared in accordance with the protocol provided in Examples 3 and 4 of U.S. application Ser. No. 07/744,649, filed Aug. 8, 1991. The product MALIGNIN is further isolated from contaminants of the crude fraction using thin layer gel (TLG) chromatography as follows:

The apparatus used is the commercially available one designed by Boehringer Mannheim GmbH; Pharmacia Fine Chemicals and CAMAG (Switzerland). The resin is 2.5 g of SEPHADEX G-200 superfine prepared in 85 ml of 0.5 M NaCl in 0.02 M $Na_2HPO_4KH_2PO_4$ Phosphate Buffer pH 6.8 (6.6-7.0). Allow to swell two or three days at room temperature with occasional gentle mixing. (Magnetic and other stirrers should not be used). The swollen gel is stabilized for three weeks at refrigerator temperatures; however, bacterial and fungal growth may interfere with the swollen gel. If the gel is to be kept for longer periods of time, a small amount of a bacteriostatic agent should be added (sodium Azide 0.02%). 2.5 g. of dry gel are used to make two 20×20 cm. glass plates of 0.5 mm. thick. The plates are either allowed to dry at room temperature for 10 minutes and transferred to a moist chamber where they can be stored for about two weeks, or they are used immediately after appropriate pre-equilibration. (Usually during the night for a minimum of 12 hours). The main function of equilibration is to normalize the ratio between the stationary and mobile phase volumes. With the pre-equilibrated plates in a horizontal position, substances to be determined are applied with micro-pipettes as spots or as a streak at the start line. 10 ml. to 20 ml. of 0.2-2% protein solution is placed on the edge of a microscopic cover slide (18 by 18 mm.) and held against the gel surface. In a few seconds the solution will soak into the gel. All samples are first prepared on the cover slides and then quickly applied. If not enough material is used, it is difficult to locate individual spots after separation. If too much material is applied no defined separation occurs. The samples are diluted with buffer for easier handling and the separation of samples is carried in a descending technique with the plate at an angle of 22°. The flow rate of about 1-2 cm/hour is most suitable. Marker substances (such as cytochrome C, hemoglobin, myoglobin or bromophenol blue labeled albumin) are applied at different positions across the plate and also to serve as reference proteins for calculation of relative distance (mobility) of unknowns. After application of samples, the plates are replaced in the apparatus and the paper wick pushed slightly downwards to ensure good contact with the gel layer. The paper wick must not drip. Excess moisture is wiped off. The liquid solvent in the reservoir is kept constant at 1 cm. from the upper end of the vessel. The runs are usually completed in 4 to 7 hours depending on the progress of separation. With colored substances separation follows directly. The separated spots of protein are easily made visible by transferring them to a paper sheet replica of the TLG plate after the chromatographic separation has been completed, and by staining them on the prewashed methanol+$H_2O$ acetic acid–90:5:5, for 48 hours. The paper sheet is 3 mm. filter paper. A sheet of paper 20×18 cm. is placed over the gel layer and pressed (rolled) just enough to ensure contact with the gel. Care is taken not to trap air under the paper (replica) and not to disturb the gel layer. The liquid phase is soaked off from the gel layer by the paper and removed after about one minute, immediately dried in an oven at 600 temperature for 15 minutes and stained in the normal way with any of the routine staining procedures. Staining is performed by spraying the replica-paper with 0.03% diazotized sulfanilic acid in 10% Sodium Carbonate (Pauley's Reagent). Staining can also be accomplished with a saturated solution of Amido Black in Methanol-Acetic acid (90:10 v/v is used); the staining time is 5-10 minutes. For destaining, rinse with two volumes of the 90:10 methanol and acetic acid solution mixed with one volume of $H_2O$. It is difficult to obtain low background staining without very extensive washing. The plates themselves may also be dried at about 60° C. (in an oven with air circulation) but only if the MALIGNIN is to be stained. For isolation purposes, the plate should only be air dried at room temperature. Over-heating can lead to cracking, but this can usually be avoided with a 50°-60° C. temperature which dries a SEPHADEX G-200 plate in 15-30 minutes. The dry plates are allowed to swell for 10 minutes in a mixture of methanol+$H_2O$+acetic acid (75: 20:5) and stained in a saturated Amido Black in the same solvent system for five hours and subsequently washed by bathing for two hours in the same solvent before they are dried. For molecular weight determinations, the distance from the starting line to the middle of each zone is measured with an accuracy of 0.05 mm. either directly on the print (replica) or on the densitogram. The result is expressed by the $R_m$ value defined as the ratio of the migration distance of the tested protein ($d_p$) to that of cytochrome C or myoglobin ($d_m$) which is used as the reference protein: Relating migration distance of tested substance to standard is the formula ($-R_m=d_p/d_m$). A straight calibration line is obtained by plotting the logarithm of the molecular weight of the standards used against the $R_m$. From this line, the molecular weight of the unknown protein can be obtained. For most exact results mix equal parts of the protein sample solution with standard, in this case cytochrome C, before applying to the plate.

In the above-described TLG step, the product MALIGNIN is observed as a discrete spot at a distance of approximately 0.91±0.02 with reference to the standard cytochrome C, yielding an approximate molecular weight of 10,000 for MALIGNIN.

The product MALIGNIN, which has been produced at this stage, is soluble in distilled water, soluble at neutral or acid pH, and insoluble at alkaline pH and having a spectrophotometric absorption peak of 280 mu. It is a polypeptide with molecular weight of approximately 10,000.

The molecular weights of MALIGNIN produced in fermentation cultures stabilized in successive generations of the cultures as shown by the thin layer gel chromatography determination are set forth in Table Example 12 below. The reproducibility of the molecular weight determination is remarkable in view of the inherent limitation of TLG chromatography.

TABLE EXAMPLE 12

Reproducibility of Molecular weight of MALIGNIN produced

| Run No. | Mol. Wt. | Run No. | Mol. Wt. | Run No. | Mol. Wt. |
|---|---|---|---|---|---|
| 1 | 9,500 | 9 | 10,100 | 17 | 10,180 |
| 2 | 8,900 | 10 | 10,180 | 18 | 10,190 |
| 3 | 10,000 | 11 | 10,180 | 19 | 10,190 |
| 4 | 10,050 | 12 | 10,180 | 20 | 10,180 |
| 5 | 10,100 | 13 | 10,180 | 21 | 10,000 |
| 6 | 10,000 | 14 | 10,050 | 22 | 9,500 |
| 7 | 10,150 | 15 | 10,180 | 23 | 10,180 |
| 8 | 12,500 | 16 | 10,190 | | |

MALIGNIN'S covalently linked amino acids are shown by hydrolysis with 6N HCL then quantitative determination to have the following average composition of amino acids:

| Amino Acid | Approximate Number of Residues |
|---|---|
| Aspartic acid | 9 |
| Threonine | 5 |
| Serine | 5 |
| Glutamic acid | 13 |
| Proline | 4 |
| Glycine | 6 |
| Alanine | 7 |
| Valine | 6 |
| ½ Cysteine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
| Approximate Total | 89 |

The molecular weight of MALIGNIN as determined by repeat Thin Layer Gel chromatography was about 10,000. The molecular weight of MALIGNIN as determined by calculation using the amino acid composition set forth above is 10,067 or about 10,000 upon rounding.

EXAMPLE 13

Production of RECOGNIN M

Malignant cells grown in tissue culture, a mammary carcinoma cell line designated MCF-7 were obtained from Mason Research Institute, Rockville, Md.

Approximately 1 gm of packed cells of MCF-7 was not further propagated upon receipt but extracted immediately and Recognin was produced according to the protocol used for producing MALIGNIN from glioma cells set forth in Examples 3 and 4 of U.S. application Ser. No. 07/744,649, filed Aug. 8, 2009. Thus, the entire medium plus cells was transferred to centrifuge tubes with cold 0.005 M phosphate buffer, pH 7, and centrifuged at 3,000 rpm in the cold for 10 minutes, the medium discarded, the cells washed twice with cold buffer, centrifuged again twice as before, and the washings discarded. The washed cells were suspended in the same buffer and disrupted by sonification for 20 seconds. The cell residues were centrifuged at 30,000 rpm for 30 minutes, the solubilized protein in the supernatant decanted and collected, and the cell residues sonified twice more, until no further appreciable protein was solubilized. The solubilized protein was concentrated and the Recognin cloven and purified by CELLEX D (BioRad) and SEPHADEX 200 (Pharmacia) gel chromatography. The yield, molecular weight, amino acid composition, behavior on thin layer gel chromatography and immunological properties of this polypeptide is similar to those of MALIGNIN as described above in Example 12. The yield in the case of MCF-7 cells was approximately 1 mg/g wet weight of cells.

The covalently linked amino acids of Recognin M are shown, by hydrolysis (in vacuo) with 6N HCL at 108° C. for 12 hours followed by quantitative automatic determination, to have the following average composition of amino acids (the nearest integer for the mole number of each amino acid is the average of two separate determinations):

| Amino Acid | Approximate Number of Residues |
| --- | --- |
| Threonine | 5 |
| Serine | 5 |
| ½ Cysteine | 1 |
| Methionine | 1 |
| Valine | 6 |
| Isoleucine | 4 |
| Phenylalanine | 3 |
| Lysine | 6 |
| Histidine | 2 |
| Arginine | 5 |
| Aspartic acid | 9 |
| Glutamic acid | 11 |
| Leucine | 8 |
| Tyrosine | 2 |
| Proline | 4 |
| Glycine | 9 |
| Alanine | 9 |
| Approximate Total | 90 |

The molecular weight of Recognin M as determined by Thin Layer Gel chromatography was about 8,000. The molecular weight of Recognin M as determined by calculation using the amino acid composition set forth above is 9,870 or about 10,000 upon rounding.

What is claimed is:

1. A method for inhibiting the growth or proliferation of glioma cancer cells in a subject suffering from glioma wherein said glioma cancer cells express malignin, said method comprising administering to said subject an effective amount of a first dosage of a composition comprising malignin wherein said administration of said dosage stimulates the immune system of said subject to produce and release anti-malignin antibody that binds and inhibits said glioma cancer cells and wherein said malignin is a polypeptide of approximately 10,000 Daltons isolated from glioma cancer cells and wherein said polypeptide has an amino acid composition of about 9 aspartic acid residues, about 5 threonine residues, about 5 serine residues, about 13 glutamic acid residues, about 4 proline residues, about 6 glycine residues, about 7 alanine residues, about 6 valine residues, about ½ of a cysteine residue, about 2 methionine residues, about 4 isoleucine residues, about 8 leucine residues, about 3 tyrosine residues, about 3 phenylalanine residues, about 6 lysine residues, about 2 histidine residues, and about 5 arginine residues and wherein said malignin elutes at a discreet spot of approximately 0.91±0.02 with reference to a standard of cytochrome C on a thin layer chromatogram when chromatographed on a plate of superfine SEPHADEX G-200 with a mobile phase of 0.5 M NaCl in 0.02 M $Na_2HPO_4KH_2PO_4$ phosphate buffer having a pH between 6.6 and 7.0.

2. The method of claim 1 wherein the composition is administered as an approximately 1 mg dosage form.

3. The method of claim 1 further comprising administering a second dose of the composition ten days after administration of the first dosage.

4. The method of claim 3 further comprising administering a third dose of the composition ten days after administration of the second dosage.

5. A method for inhibiting the growth or proliferation of breast cancer cells in a subject suffering from breast cancer wherein said breast cancer cells express Recognin-M, said method comprising administering to said subject an effective amount of a first dosage of a composition comprising Recognin-M wherein said administration of said dosage stimulates the immune system of said subject to produce and release anti-Recognin-M antibody that binds and inhibits said breast cancer cells and wherein said Recognin-M is a polypeptide of approximately 10,000 Daltons isolated from MCF-7 cells and wherein said polypeptide has an amino acid composition of about 5 threonine residues, about 5 serine residues, about ½ of a cysteine residue, about 1 methionine residue, about 6 valine residues, about 4 isoleucine residues, about 3 phenylalanine residues, about 6 lysine residues, about 2 histidine residues, about 5 arginine residues, about 9 aspartic acid residues, about 11 glutamic acid residues, about 8 leucine residues, about 2 tyrosine residues, about 4 proline residues, about 9 glycine residues, and about 9 alanine residues, and wherein said Recognin-M elutes at a discreet spot of approximately 0.9 with reference to a standard of cytochrome C on a thin layer chromatogram when chromatographed on a plate of superfine SEPHADEX G-200 with a mobile phase of 0.5 M NaCl in 0.02 M $Na_2HPO_4KH_2PO_4$ phosphate buffer having a pH between 6.6 and 7.0.

* * * * *

UNITED STATES PATENT AND TRADEMARK OFFICE
CERTIFICATE OF CORRECTION

PATENT NO.       : 7,658,935 B2                                          Page 1 of 1
APPLICATION NO.  : 09/854568
DATED            : February 9, 2010
INVENTOR(S)      : Samuel Bogoch It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1089 days.

Signed and Sealed this

Thirtieth Day of November, 2010

David J. Kappos
*Director of the United States Patent and Trademark Office*